US00PP14276P29

(12) United States Plant Patent

Hanes

(10) Patent No.: US PP14,276 P2
(45) Date of Patent: Nov. 4, 2003

(54) PETUNIA PLANT NAMED 'WHIP DARSAL'

(50) Latin Name: *Petunia hybrida*
Varietal Denomination: Whip Darsal

(75) Inventor: Mitchell Eugene Hanes, Morgan Hill, CA (US)

(73) Assignee: Goldsmith Seed Inc., Gilroy, CA (US)

( * ) Notice: Subject to any disclaimer, the term of this patent is extended or adjusted under 35 U.S.C. 154(b) by 0 days.

(21) Appl. No.: 10/389,099

(22) Filed: Mar. 13, 2003

(51) Int. Cl.[7] ..... A01H 5/00
(52) U.S. Cl. ..... Plt./356
(58) Field of Search ..... Plt./356

*Primary Examiner*—Kent Bell
(74) *Attorney, Agent, or Firm*—Jondle & Associates P.C.

(57) ABSTRACT

A petunia cultivar particularly distinguished by small dark salmon colored flowers, compact habit and good basal branching.

1 Drawing Sheet

Genus and species: *Petunia hybrida.*
Variety denomination: 'Whip Darsal'.

BACKGROUND OF THE NEW PLANT

The present invention comprises a new and distinct cultivar of petunia, botanically known as *Petunia hybrida,* and hereinafter referred to by the cultivar name 'Whip Darsal'. The new cultivar is asexually reproduced from vegetative cuttings and tissue culture resulting from the cross of the seed/pod parent 00-382-4, a single purple proprietary line that is unnamed and unpatented×00-381-2, a single scarlet proprietary line that is unnamed and unpatented.

'Whip Darsal' is a product of a planned breeding program intended to create new petunia plants with a small dark salmon colored flowers, compact habit, good basal branching and moderately vigorous growth.

The new cultivar was created in 2000 in Gilroy, Calif. and has been asexually reproduced repeatedly by vegetative cuttings and tissue culture in Gilroy, Calif., Andijk, The Netherlands, and Guatemala over a two-year period. The plant has also been trialed at Gilroy, Calif., Litchfield, Mich. and Andijk, The Netherlands. The present invention has been found to retain its distinctive characteristics through successive asexual propagations; and this novelty is firmly fixed.

DESCRIPTION OF PHOTOGRAPH

This new petunia plant is illustrated by the accompanying photograph which shows blooms, buds, and foliage of the plant in full color, the colors shown being as true as can be reasonably obtained by conventional photographic procedures.

The photograph shows the mature flowers.

DESCRIPTION OF THE NEW CULTIVAR

The following detailed descriptions set forth the distinctive characteristics of 'Whip Darsal'. The data, which defines these characteristics, were collected from asexual reproductions carried out in Gilroy, Calif. The plant history was taken on 6 months old plants grown in one-gallon pots in fall/winter season, in a poly-covered greenhouse under 2–4 hours supplemental light and color readings were taken in the greenhouse in the winter season under natural light.

Plants had been cut back numerous times prior to data readings being taken. Color references are primarily to The R.H.S. Colour Chart of The Royal Horticultural Society of London (R.H.S.). Texture description details were observed under a dissecting microscope according to The New Royal Horticultural Society Dictionary of Gardening (1992).

THE PLANT

Classification:
*Botanical.*—*Petunia hybrida.*
*Commercial.*—Petunia.
Form: Semi upright and decumbent.
Growth and branching habit: Good vigorous habit, well-branched, full plant.
Height: From soil level to top of blooms.—Approximately 10–20 cm.
Width: Approximately 45–60 cm including flowers.
Time to produce a finished flowering plant.—9–11 weeks.
Outdoor plant performance: Full sun, free-flowering through the summer, some heat tolerance. Use in hanging baskets, mixed containers, window boxes and mass plantings.
Time to initiate roots: Approximately 18–23 days in the greenhouse.
Root description: Fibrous, white.

THE LEAVES

Arrangement: Alternate, upper leaves sub-opposite.
Length: 4.3–4.8 cm.
Width: 2.7–3.3 cm.
Leaf blade shape: Cordate.
Leaf margin: Entire.
Apex aspect: Acute.
Base aspect: Acuminate.
Leaf color: Upper side; RHS 137B (green); Underside; RHS 138A (green).
Texture: Short glandular hairs.
Venation: Palmate.
Venation color: RHS 144C (yellow-green).
Petiole length: 0.8–1.0 cm.
Petiole width: 0.2 cm.
Petiole color: RHS 144C (yellow-green).
Petiole texture: glandular hairs of various sizes.

THE STEM

Length: 25–40 cm.
Diameter: 2.0–4.0 cm.
Internode length: 1.5–4.0 cm.
Color: RHS 144A (yellow-green).
Texture: Glandular hair of various sizes.
Stem anthocyanin: None.
Peduncle color: RHS 144B (yellow-green).
Peduncle length: 4.3–4.5 cm.
Peduncle diameter: 1.0 cm.
Peduncle texture: Many glandular hairs of various sizes.

THE BUD

Shape: Oblong.
Diameter: 0.5 cm.
Length: 1.5–3.0 cm.
Color at tight bud: RHS 145B (yellow-green) with RHS 146C (yellow-green) mid-veins.

THE FLOWER

Blooming habit: Continuous all through the growing season. Good floriferousness.
Inflorescence type: Flowers solitary in upper leaf axis.
Young flower color: RHS 46B (red).
Young flower-Floret diameter:3.3–3.7 cm.
Mature flower color: Front side, between RHS 46C/D (red); RHS 46A (red) mid-veins; slight blotching of shades of RHS 46B (red) throughout petals flower/petal color. Underside, RHS 38D (red); RHS 152B/C (yellow-green) mid-veins.
Corolla tube color inside: RHS 161D (greyed-yellow); RHS 165 (greyed-orange) veining.
Corrolla tube length: 2.0–2.2 cm.
Corolla outside texture: Many long glandular hairs.
Floret form and number of petals: Funnel form, 5 lobed petals (single type) fused at base.
Flower (limb) diameter: 3.9–4.2 cm.
Petal apex shape: Acute.
Petal margin: Entire.
Petal waviness (ruffle of petal): Weak.
Petal lobation: Weak-Moderate.
Petal texture: Papillose.
Calyx: 5 deeply lobed sepals, fused at base.
Sepal color: RHS 137B (green).
Sepal length: 1.8–2.5 cm.
Sepal width: 0.4–0.5 cm.
Sepal shape: Oblong.
Sepal apex: Acute-Obtuse.
Sepal texture: Short glandular hairs of various sizes.
Lastingness of individual blooms: 4–8days.
Fragrance: None.

THE REPRODUCTIVE ORGANS

Stamens: Five, 2 taller and 3 shorter.
Filament color: RHS 155C (white).
Pollen color: RHS 155A (white).
Pistil: One.
Stigma: RHS 144B (yellow-green).
Style color: RHS 145C (yellow-green).
Fruit seed set: Not observed.

DISEASE AND INSECT RESISTANCE

Not observed.

COMPARISON WITH KNOWN CULTIVARS

Compared to its female parent 00-382-4 in the following ways: The female parent has a purple flower compared to the 'Whip Darsal'. The female is earlier to flower.

Compared to its male parent 00-381-2 in the following ways: The male parent has a scarlet large flower compared to the 'Whip Darsal', which has a small dark salmon flower color. The male parent also is later to flower.

I claim:

1. A new and distinct petunia plant as shown and described herein.

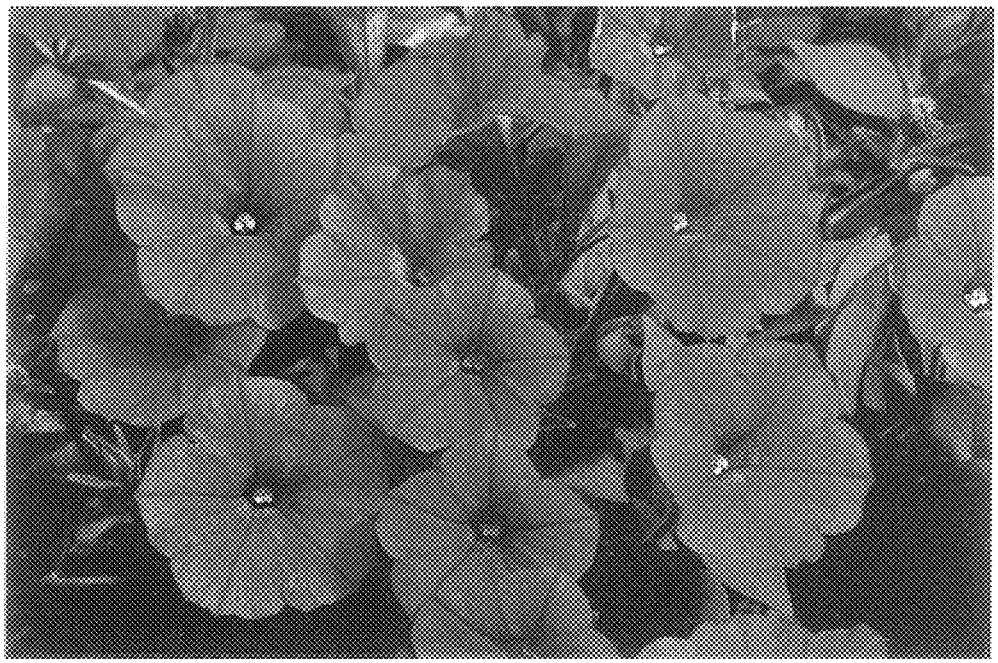

* * * * *